(12) United States Patent
Kelly

(10) Patent No.: US 7,861,709 B2
(45) Date of Patent: Jan. 4, 2011

(54) APPARATUS FOR WARMING A USER AND KEEPING A USER WARM, A SYSTEM, AND A METHOD

(76) Inventor: Teresa Goodman Kelly, 57 Camelot Dr., West Milford, NJ (US) 07480

( * ) Notice: Subject to any disclaimer, the term of this patent is extended or adjusted under 35 U.S.C. 154(b) by 234 days.

(21) Appl. No.: 11/752,158

(22) Filed: May 22, 2007

(65) Prior Publication Data

US 2007/0277804 A1    Dec. 6, 2007

Related U.S. Application Data

(60) Provisional application No. 60/747,922, filed on May 22, 2006.

(51) Int. Cl.
*A61F 7/00* (2006.01)
*A41D 5/00* (2006.01)
*F24J 1/00* (2006.01)

(52) U.S. Cl. ............... 126/204; 126/263.01; 126/208; 2/69

(58) Field of Classification Search ........... 126/204, 126/208, 263.01
See application file for complete search history.

(56) References Cited

U.S. PATENT DOCUMENTS

| | | | | |
|---|---|---|---|---|
| 586,998 | A * | 7/1897 | Harmer | 126/206 |
| 1,272,394 | A * | 7/1918 | Devney | 40/331 |
| 1,380,480 | A * | 6/1921 | Jennings | 5/490 |
| 1,602,941 | A * | 10/1926 | Rosman | 5/485 |
| 1,670,460 | A * | 5/1928 | Leibold | 5/413 R |
| 2,346,998 | A * | 4/1944 | Reveno | 126/204 |
| 2,413,828 | A * | 1/1947 | Hirsh et al. | 5/485 |
| 3,329,971 | A * | 7/1967 | Shelby | 2/69 |
| 3,443,066 | A * | 5/1969 | Weibel | 219/527 |
| 3,554,156 | A * | 1/1971 | Kishida et al. | 116/28.1 |
| 3,835,471 | A * | 9/1974 | Lankford | 2/84 |
| 4,035,606 | A * | 7/1977 | Browder | 219/211 |
| 4,241,721 | A * | 12/1980 | Holly | 126/204 |
| 4,573,447 | A * | 3/1986 | Thrash et al. | 44/251 |
| 4,604,987 | A * | 8/1986 | Keltner | 126/204 |
| D343,088 | S | 1/1994 | Owens | |
| 5,300,105 | A | 4/1994 | Owens | |

(Continued)

OTHER PUBLICATIONS

Information about Microcore Heated Seat Cushions, www.kitchenkapers.com, Kitchen Kapers Inc., Copyright 2009.

(Continued)

*Primary Examiner*—Carl D Price
(74) *Attorney, Agent, or Firm*—Christopher D. Goodman

(57) ABSTRACT

Embodiments of the present invention provide an apparatus including a heat source, a covering, and a transportable case. The a transportable case may be sized and shaped to enclose the heat source and the covering in thermal transfer relation to warm the covering while the covering is in a first state. The covering may also have a second state, after being heated by the heat source in the first state wherein it may be at least partially wrapped around a user to partially warm the user from the heat provided thereto in the first state. The covering may be formed into a canopy-like form, in the second state, being substantially enclosed at a top and wherein the heat source may be positioned in relation to the canopy-like form to provide heat to within the canopy-like form.

14 Claims, 4 Drawing Sheets

U.S. PATENT DOCUMENTS

| | | | | |
|---|---|---|---|---|
| 5,398,667 | A * | 3/1995 | Witt | 126/263.01 |
| 5,405,186 | A * | 4/1995 | Hanson et al. | 297/180.1 |
| 5,500,010 | A | 3/1996 | Owens | |
| 5,545,198 | A * | 8/1996 | Owens | 607/108 |
| 5,551,108 | A * | 9/1996 | Butler, III | 5/655 |
| 5,572,753 | A * | 11/1996 | Ruscitto | 5/490 |
| 5,738,082 | A * | 4/1998 | Page et al. | 126/263.01 |
| 5,750,962 | A | 5/1998 | Hyatt | |
| 5,884,331 | A * | 3/1999 | Barajas | 2/69 |
| 6,007,572 | A | 12/1999 | Baldwin | |
| 6,329,644 | B1 | 12/2001 | Hyatt | |
| 6,353,933 | B1 * | 3/2002 | Love | 2/88 |
| 6,827,080 | B2 * | 12/2004 | Fish et al. | 126/263.01 |
| 6,886,553 | B2 | 5/2005 | Yim | |
| 6,918,138 | B2 * | 7/2005 | Donovan | 2/174 |

OTHER PUBLICATIONS

Vesture Microcore Lava Buns and Heated Seat Cushions, www.kitchenkapers.com, Kitchen Kapers Inc., Copyright 2009.

* cited by examiner

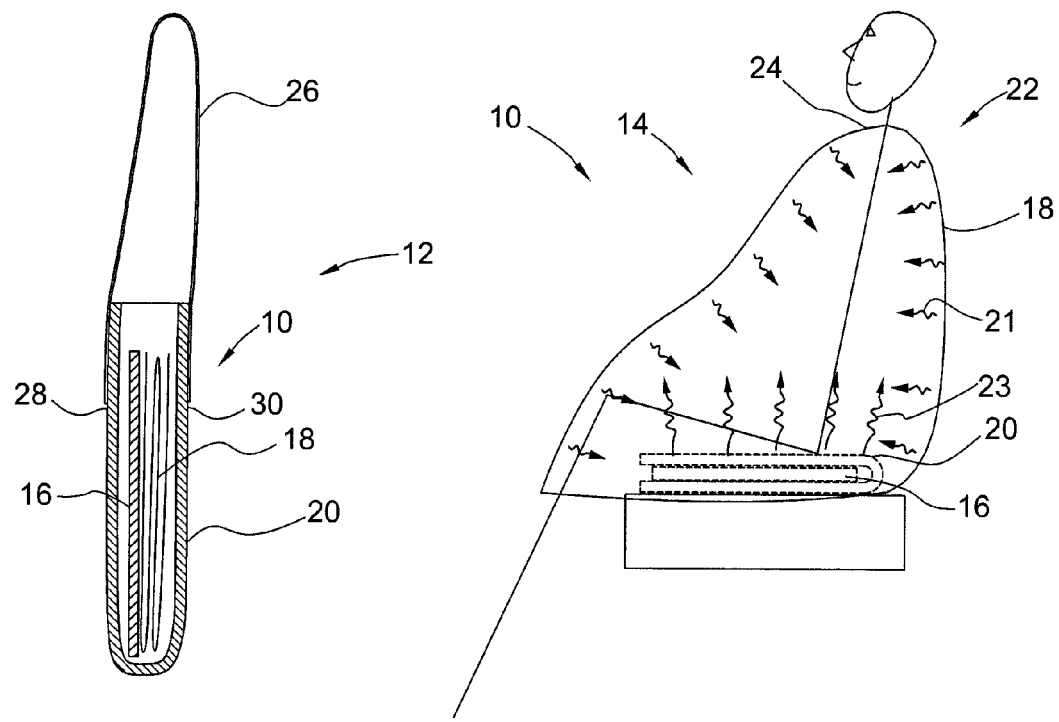
FIG. 1A
FIG. 1B
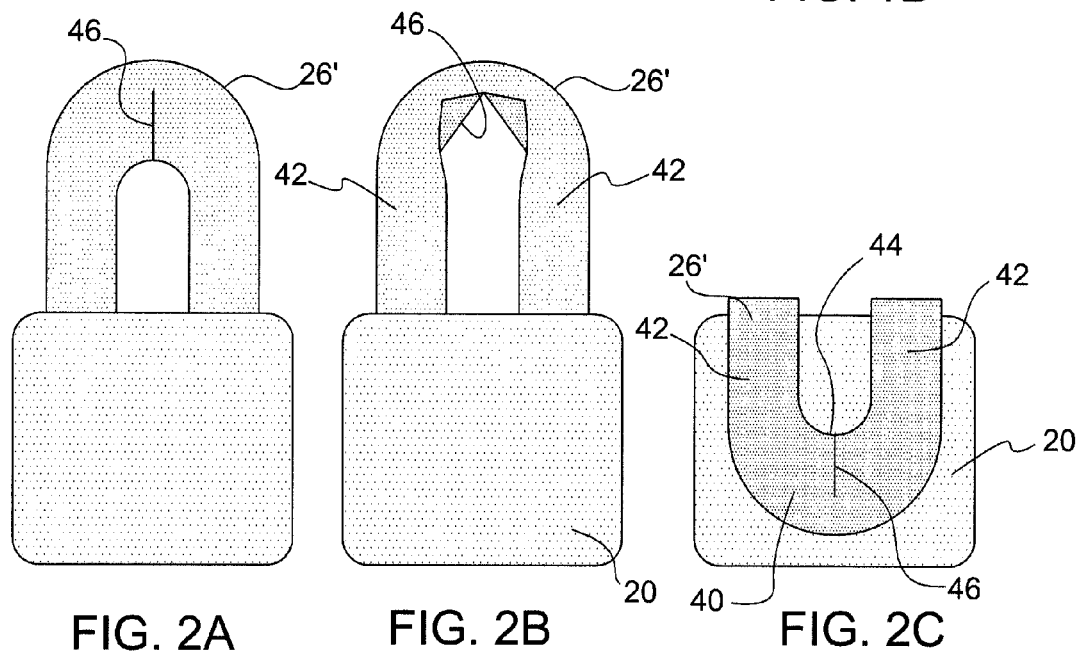
FIG. 2A
FIG. 2B
FIG. 2C

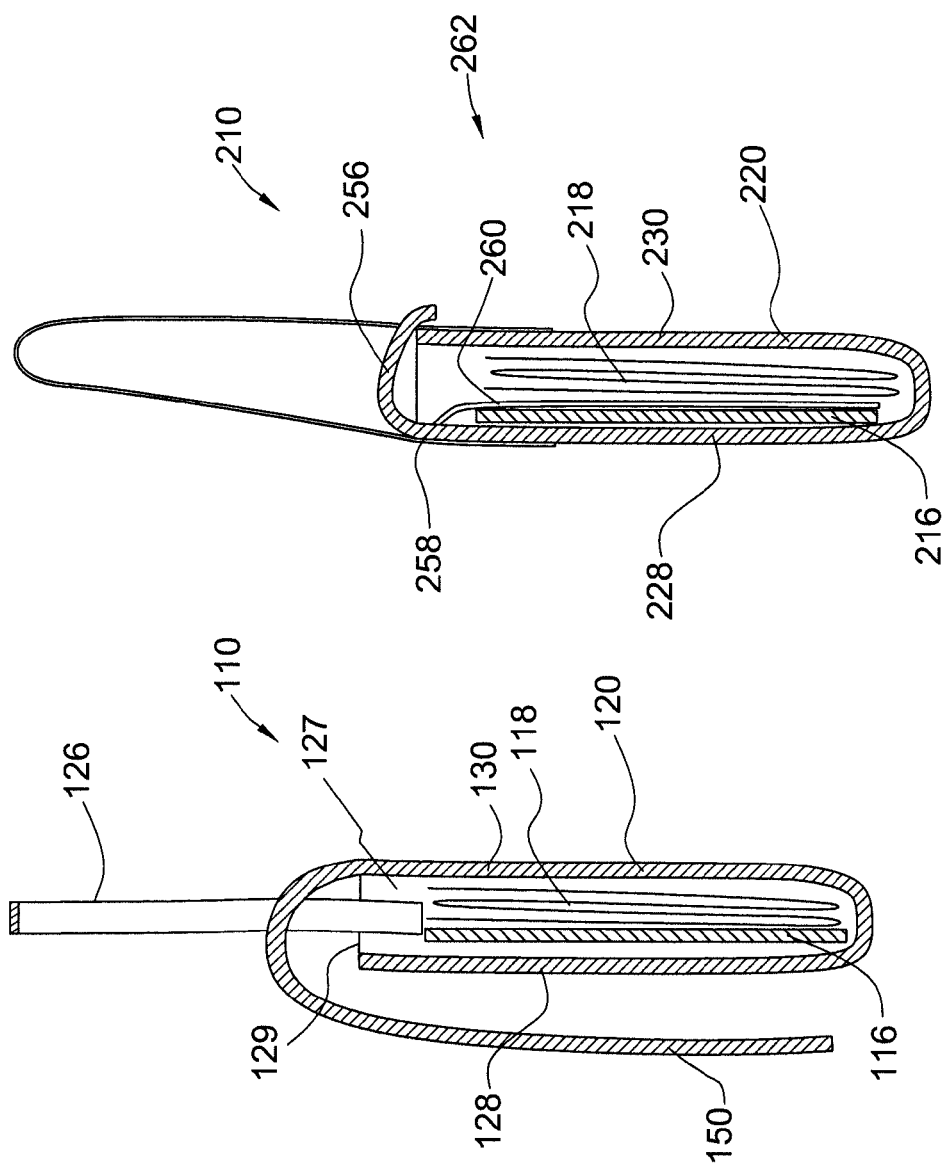

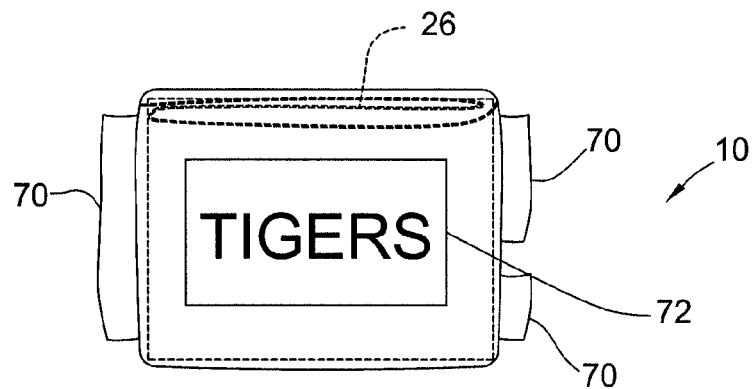
FIG. 6
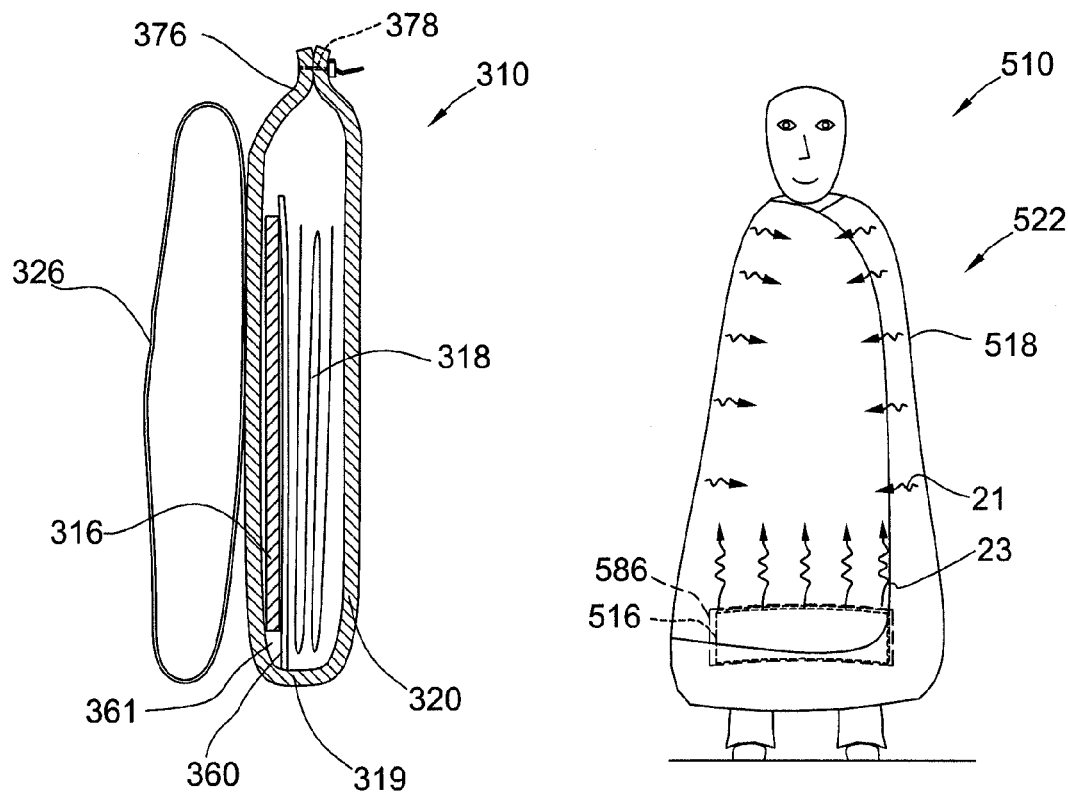
FIG. 7
FIG. 9

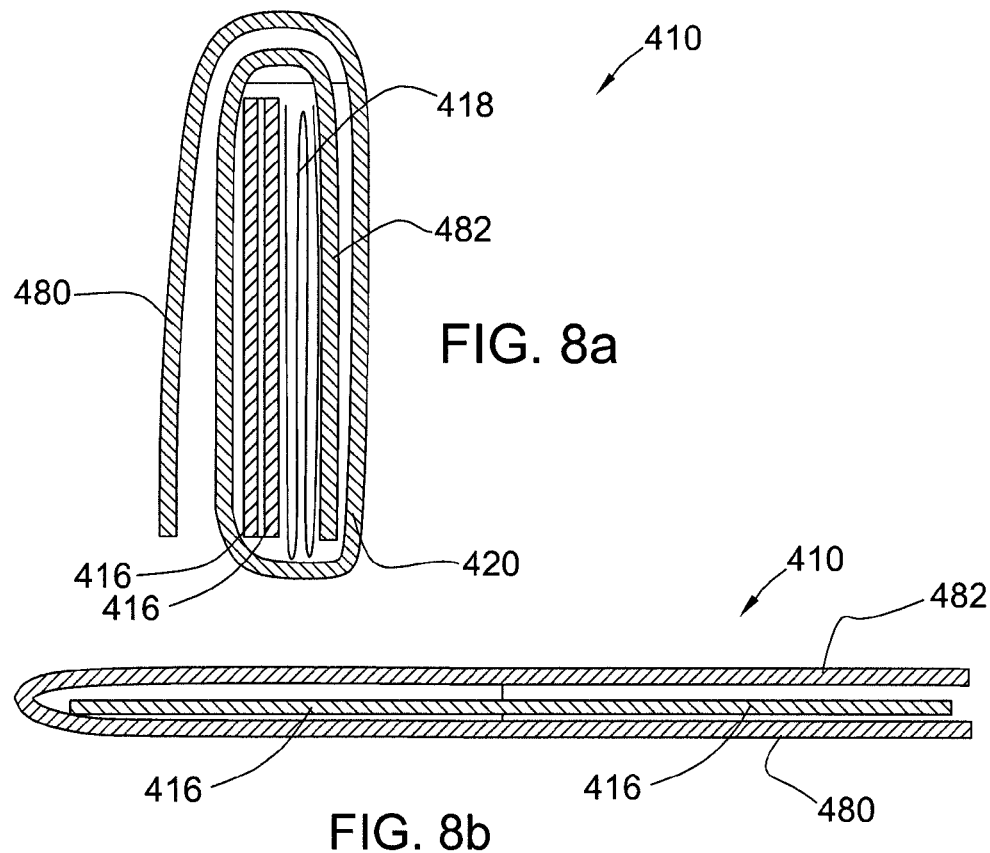
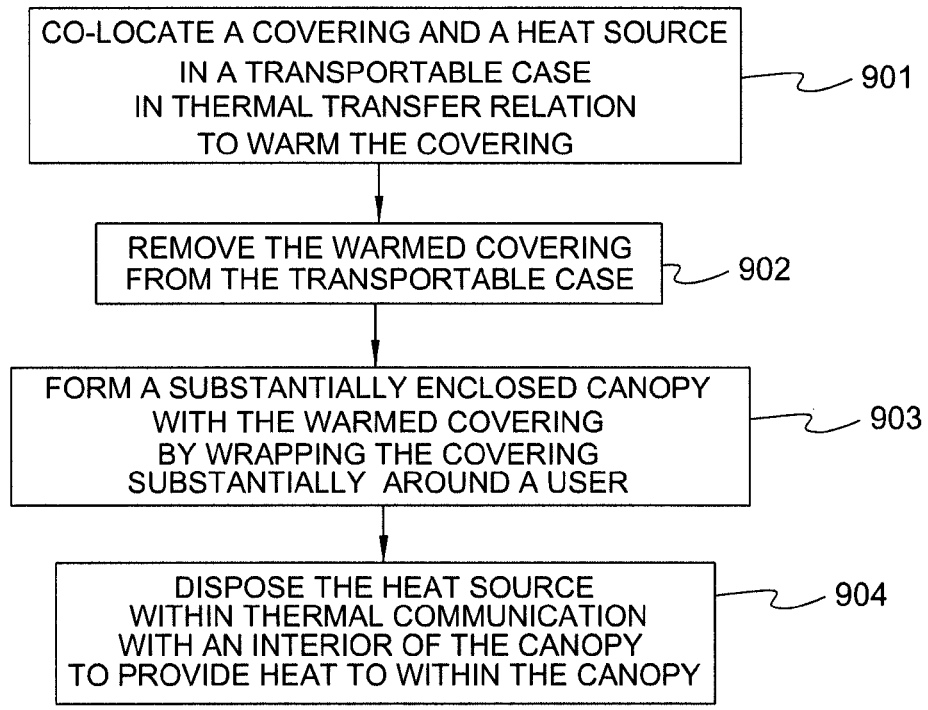

APPARATUS FOR WARMING A USER AND KEEPING A USER WARM, A SYSTEM, AND A METHOD

CROSS REFERENCE TO RELATED APPLICATIONS

The present application is a continuation-in-part of and claims priority to U.S. Patent Application No. 60/747,922, filed May 22, 2006, entitled "AN APPARATUS FOR WARMING AND TRANSPORTING A BLANKET, SYSTEM, AND METHOD," the entire disclosure of which is hereby incorporated by reference in its entirety.

TECHNICAL FIELD

The present invention relates to the field of warming devices, and in particular to a transportable arrangement for warming a user and keeping the user warm.

BACKGROUND

Millions of people attend events wherein the temperature of the venue is uncomfortably cold, in particular outdoor events. Oftentimes a spectator will bring a blanket to the event; however, transporting the blanket in a cold environment and/or in a cold car to the event until the spectator finds his or her seat often makes the blanket cold, and until the blanket and the space below the blanket warms up the spectator may be uncomfortably cold. In addition, once the spectator finds his or her seat it is often on a cold bench, a cold bleacher, or on the cold ground. Sitting on cold surfaces is typically uncomfortable.

During exertion, for example, while walking to one's seat, the spectator will generate body heat, and is usually dressed appropriately to stay comfortable while moving. Heat lost through a person's clothing will more or less reach equilibrium with the body heat generated while moving. Once stopped however, for example, while sitting and watching an event, the person's body temperature will drop. The person will often subsequently get uncomfortably cold. If the person wraps a cold blanket around themselves while sitting, the heat transfer from the person's clothing will temporarily increase as it is conducted to the cold blanket. The body temperature of the person may drop, and may not be easily brought back up to a comfortable level. Even if brought eventually up to a comfortable level, the energy expended to warm a cold blanket, and the space below the blanket, may hasten an eventual chill.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 1A illustrates a cross sectional view of an apparatus in a first state and FIG. 1B illustrates a schematic side view of the apparatus in a second state in accordance with various embodiments of the invention;

FIGS. 2A, 2B, and 2C illustrate front views of an embodiment in three positions thereof;

FIG. 3 is a cross sectional view illustrating various embodiments in accordance with the invention;

FIG. 4 and FIG. 5 are cross sectional views illustrating various embodiments in accordance with the invention;

FIG. 6 is a front view of an apparatus in accordance with various embodiments of the invention;

FIG. 7 is a cross sectional view illustrating various embodiments in accordance with the invention;

FIGS. 8a and 8b are sectional views illustrating various embodiments in accordance with the invention in respective first and second positions;

FIG. 9 is front view illustrating somewhat schematically an embodiment in accordance with the invention wherein a user may create a canopy, or tent-like structure by wrapping a covering around themselves while standing; and FIG. 10 is a flow diagram illustrating various embodiments in accordance with the invention.

DESCRIPTION OF THE PREFERRED EMBODIMENTS

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" means A or B. For the purposes of the description, a phrase in the form "A and/or B" means "(A), (B), or (A and B)." For the purposes of the description, a phrase in the form "at least one of A, B, and C" means "(A), (B), (C), (A and B), (A and C), (B and C), or (A, B and C)." For the purposes of the description, a phrase in the form "(A)B" means "(B) or (AB)," that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

Embodiments may provide an apparatus, system, and/or a method including a covering and a heat source being co-housed within a transportable case in a first state and which may be used to create a warmed and a warming canopy in a second state. The term canopy should be understood in a broad sense and may be understood to refer to a barrier being substantially concave down and effective to at least partially slow or prevent convective heat transfer therethrough. The term tent-like structure may also be used. The term "a user" may refer to one or more users.

Embodiments of the present invention may provide a transportable warming and sheltering apparatus wherein a user may minimize body heat loss upon initial use of a warmed cover, and use the same source of heat used to warm the cover to keep a space under the cover warm.

Embodiments of the present invention may provide a tent-like form heated at or near the bottom thereof and suitable to be sat upon wherein the walls of the tent are warmed and the inside of the tent may be kept warm with a single heat source.

Embodiments in accordance with the invention may provide a warmed canopy and a canopy for holding the warmth around a user.

Embodiments may provide a combination of a heated canopy and a heat source within or thermally coupled with the canopy that may delay or prevent an eventual chill and provide extended comfort to the user at an event. Embodiments in accordance with the invention avoid the thermal transfer of heat away from the user upon being covered with a cold covering. Embodiments may enable a user in a cold environment to maintain a greater core temperature for an extended period of time, stay comfortable longer and avoid being chilled.

Embodiments may be compact, efficient, and easily transported. In various embodiments a case may serve to insulate a heating element while in the transportable encasement conserving heat while being transported and providing more heat when needed.

FIG. 1A illustrates a cross sectional view of an apparatus 10 in a first state 12 and FIG. 1B illustrates a schematic side view of the apparatus 10 in a second state 14 in accordance with various embodiments of the invention. The apparatus 10 may include a heat source 16, and a covering 18. The apparatus 10 may also include a transportable case 20 sized and shaped to enclose the heat source 16 and the covering 18 in thermal transfer relation to warm the covering 18 while the covering 18 is in the first state 12. The covering 18 also has a second state 14, after being heated by the heat source 16 in the first state 12, and being at least partially wrapped around a user to partially warm the user from the heat provided thereto in the first state 12 and formed into a canopy-like form 22 being substantially enclosed at a top 24, and wherein the heat source 16 is positioned in relation to the canopy-like form 22 to provide heat to within the canopy-like form 22. Heat from the covering 18 is represented in FIG. 1B with arrows 21. Heat from the heat source 16 is represented with arrows 23.

Various embodiments may provide a system including a fabric being of a size and shape suitable to be at least partially wrapped around a user and to be formed into a tent-like form being substantially enclosed at a top; a heating element; and a transportable case for encasing the fabric and the heating element and for holding the fabric and the heating element in heat transferring proximity to provide a first quantity of heat to the fabric from the heating element, the fabric providing at least a portion of the first quantity of heat to the user when wrapped around the user, and the heating element positionable below or within the tent-like form such that a second quantity of heat is provided to within the tent-like form from the heating element.

The apparatus 10 may be adapted to be carried. The case 20 may be configured as a bag 20 and may include one or more handles 26 which may be adapted as straps that may be adapted to fit over the shoulder, or grasped in the hand, of a user of the apparatus 10. The case 20 may be made from an insulative material. The handle or strap 26 may be adapted to be coupled with, or attached to, a first side 28 and a second side 30 of the case 20.

The heat source 16 may be, for example, a substantially plainer flexible package enclosing a material which when heated, for example, in a microwave oven, may retain heat that may be transferred to the covering 18 while the heat source 16 and the covering 18 are in the case 20. Various embodiments may use a heat source heated through chemical means, or electrical means.

In certain situations a user may find the heat coming from the heat source through the walls of the case to be uncomfortably warm. This may be the case, for example, when the user first sits down and the heating element is at its warmest, and before it cools to a more comfortable temperature. Various embodiments may provide insulating members positionable between the heat source and the user. Starting with a cooler heat source may not be desirable because the overall heat content of the heating element may then be less than desirable.

FIGS. 2A, 2B, and 2C illustrate front views of an embodiment in three positions thereof. The case may have a handle 26' adapted to be formed into a shape substantially similar to an area of contact a person makes when sitting on a surface to provide an added insulating layer, or a heat spreading layer, between the person and the warming element while still allowing for a relatively greater heat transfer in areas immediately adjacent to the area of contact. In the illustrated embodiment the insulating layer may also be usable as a handle in a first position and usable to unsulate the buttocks and upper thighs of a user in a second position. In one embodiment while in the first position, the handle 26' may form an inverted U shape 40 with the legs 42 of the U 40 being coupled with the case 20 and the trough 44 of the U distal from the case, and while in the second position the handle 26' may be folded on top of the case 20 and adapted to be formed into a shape substantially similar to an area of contact a person makes when sitting on a surface.

In one embodiment the trough 44 of the U may include a slit 46 such that a portion of the trough may be folded, as shown in FIG. 2B, upon the body of the U-shaped handle, or strap 26' thereby extending the depth of the U and extending the effective length of the legs of and therefore the effective length of the strap the handle while being worn over a user's shoulder. The additional material from the folded portion may also make the strap 26' more comfortable when worn by the user.

FIG. 3 is a sectional view illustrating various embodiments in accordance with the invention. An apparatus 110 may include a case 120 adapted as a bag 120 having an oversized flap 150 which may extend over and provide a double layer of, insulation on a first side 128 of the case 120. A covering 118 and a second side 130 of the case 120 may together also provide multiple layers of insulation on the second side 130 of a heat source 116. Various embodiments, such as the one illustrated may include one or more handles or a straps 126 attached to the inside 127 of two opposed ends 129 of the bag (one is illustrated in the figure). The apparatus 110 with the straps 126 attached on the ends 129 may allow for the flap 150 to easily pass between the ends 129 of the strap 126 to the opposite side of the bag.

FIG. 4 and FIG. 5 are sectional views illustrating various embodiments in accordance with the invention. An apparatus 210 for warming and transporting a covering 218, may include a case 220 having a top 256 configured to enclose the case 220. A partition 260 may be attached at one end 258 to the case 220. In this example embodiment, a heat source 216 may be positioned adjacent a first side 228 of the case 220, and the covering 218 may be positioned adjacent a second side 230. In various embodiments the partition 260 may be used to control or adjust an amount of heat transfer from the heat source 216 to the covering 218. The partition 260 may be used to provide some structure to the case 220 and may be used to hold the heat source 216 in place. FIG. 3 illustrates the partition in a first position 262. FIG. 4 illustrates the partition 260 in a second position 264 wherein the covering 218 is adjacent to the heat source 216. The partition 260 then may provide additional insulation to the side of the covering 218 furthest from the heat source 216, and may provide a further enclosed environment in which the heat source 216 may provide direct heat transfer to the covering 218.

Upon arriving at an event and finding a seat, a user may remove the covering 218 from the case 220, and in some cases tuck the handle into the case 220. Then the user may place the case 220 onto the seat, sit down, then utilize the warmed covering 218 while sitting down on the warm apparatus 210. In the case of the embodiments illustrated in FIGS. 4 and 5 the user may selectively position the partition 260 to one side or the other of the heat source to regulate the heat coming therefrom, or may simply turn the bag over. The partition 260 may provide additional insulation on one side of the heat source 216 to prevent heat loss out the side and into the cold seat while fewer layers of insulation may be disposed between the user and the heat source.

In various embodiments the partition 260 may be waterproof and may be positionable to an outside of the case 220 and may protect one side of the bag if placed on, for example, a wet or soiled surface. In various embodiments the partition 260 may be removable. Various embodiments may be constructed from a machine-washable fabric. Various embodiments may include one or more portions of highly insulative material, for example, a foil, that may tend to prevent heat from being transferred to a cold surface. Various embodiments may be constructed from a waterproof material, or may be adapted to be covered with a waterproof material. Various embodiments may be adapted to be covered after having been used on a wet or soiled surface to protect the user from the wet or soiled apparatus when leaving an event. Various embodiments may include a cover that may be housed within the case until the user decides to cover it.

FIG. 6 is a front view of an apparatus 10 according to various embodiments of the invention. The apparatus 10 is illustrated with a handle 26 inside the case 20. The apparatus 10 may include pockets 70 which may be positioned on the sides thereof to allow a user to keep items in the bag without sitting on them. The apparatus 10 may be configured to include a moniker 72 identifying a local sports team or an indication of some affiliation such as a school, church, parish, or city. Various embodiments may be constructed by mass-producing larger quantities of cases 20, and may be customized or semi-customized with specified monikers 72. Various embodiments may be made in different colors which may identify similar affiliations or team preferences.

FIG. 7 is a sectional view illustrating various embodiments in accordance with the invention. An apparatus 310 may be adapted to be carried over one's shoulder backpack-style utilizing straps 326, and may include a case 320 having a top 376 closeable with, for example, a drawstring 378 around the shoulders of a user.

The example embodiment illustrated in FIG. 7 also includes a partition 360 adapted to be attached at a bottom 319 of the case 320. The partition 360 may be adapted to function similar to the partition 360 illustrated in the FIGS. 4 and 5.

The partition 360 and a side wall of the case 320 may be adapted to form a pocket 361 to hold the heat source 316. In this and various embodiments, the partition may be made from a non-insulative material, a poor insulator, or a conductive material to provide effective heat transfer from the heat source 316 to the covering 318.

FIGS. 8a and 8b are sectional views illustrating various embodiments in accordance with the invention. An apparatus 410 includes a case 420 which may include a first oversized flap 480 and a second oversized flap 482 shown in FIG. 8a respectively folded over one side of, and tucked in side of, the case 420. The first and second oversized flaps 480, 482 may provide additional layers of insulation when transporting the case 420. A heat source 416 may be an oversized or double-width heat source that may be folded inside the case 420. Various embodiments may use two heat sources of regular width. As illustrated in FIG. 8b, the apparatus 410 may be used by removing the warm covering 418, unfolding the first flap 480, and the second flap 482, unfolding the heat source 416 such that the heat source may be positioned parallel to and adjacent to the body of the case 420, and also to the unfolded flaps 480 and 482. The apparatus 410 may then be placed on a seat occupying substantially double the width as may be the case, for example, in the embodiment illustrated in FIG. 2A. Two people or a larger single person may then sit on the apparatus 410 under the covering 418. Various embodiments may be unfolded as described or in other various configurations. Various embodiments may be adapted to be long and wide enough such that a user may lie down on the apparatus warmed by the heat of the heat source, and may use the warm covering on top. Various embodiments may be utilized by, for example, campers. Various embodiments may be used in emergency or near emergency situations wherein a person has collapsed or has fallen and must be kept warm. Various embodiments may be constructed the same or similar to the embodiments illustrated in FIG. 8a but roughly one half the size described such that when unfolded as shown in FIG. 8b is as wide as a typical single seat. No scale should necessarily be inferred from the figures illustrated.

Various insulating, or partial insulating layers, or heat spreading layers, may be used to prevent overheating, or burning on various contact surfaces of a user. Such layers may be shaped similar to the contact surfaces as described in relation to the embodiments illustrated in FIGS. 2A-2C.

FIG. 9 is front view illustrating somewhat schematically various embodiments in accordance with the invention wherein a user may create a canopy 522, or tent-like structure by wrapping a covering 518 around themselves while standing. The apparatus 510 may include one or more pockets 586, or a pouch on an inside thereof to facilitate positioning a heat source 516 within the canopy 522. The heat source 516 and the covering 518 may have been co-disposed within a case (not shown) to effect heat transfer from the heat source 516 to the covering 518. Heat from the covering 18 is represented with arrows 21. Heat from the heat source 16 is represented with arrows 23. In one embodiment a user may simply stand on the heat source 516 allowing heat to rise into the canopy 522.

FIG. 10 is a flow diagram illustrating various embodiments in accordance with the invention. A method in accordance with the invention may include:

co-locating a covering and a heat source in a transportable case in thermal transfer relation to warm the covering, 901;

removing the warmed covering from the transportable case, 902;

forming a substantially enclosed canopy with the warmed covering by wrapping the covering substantially around a user, 903; and disposing the heat source within thermal communication with an interior of the canopy to provide heat to within the canopy, 904.

In various embodiments the disposing the heat source within thermal communication with an interior of the canopy may include positioning the transportable case with the heat source therein for sitting thereon and the forming the substantially enclosed canopy over a seated user.

In other embodiments the disposing the heat source within thermal communication with an interior of the canopy may include positioning the heat source in a pocket of the covering.

Methods in accordance with various embodiments may include heating up the heat source with a microwave oven prior to the co-locating. Other embodiments may include heating up the heat source with an electrical source prior to the co-locating. The electrical source may be a vehicle battery in some embodiments.

Various embodiments may further comprise folding a handle which may be coupled with the transportable case and which may be formed into a shape substantially similar to an area of contact a person makes when sitting on a surface onto the transportable case, the handle providing an added insulating layer between the person and the heat source while still allowing for a relatively greater heat transfer in areas immediately adjacent to the area of contact.

Various methods may include: heating the heat source, for example, in a microwave oven; placing the heat source in the transporting apparatus; placing the covering in the transporting apparatus; removing the covering to use as a covering; and placing the transporting apparatus for sitting.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An apparatus comprising:
   a heat source;
   a covering; and
   a transportable case adapted to be carried and sized and shaped to enclose the heat source and the covering in thermal transfer relation to warm the covering while the covering is in a first state i.e. while adapted to be carried, the covering having a second state, after being heated by the heat source in the first state, while in the second state the covering being at least partially wrapped around a user to partially warm the user from the heat provided thereto in the first state and the covering formed into a canopy-like form being substantially enclosed at a top and wherein the heat source is positioned in relation to the canopy-like form to provide heat to within the canopy-like form wherein the transportable case includes a multi position flap having a first position between the heat source and the covering and a second position wherein the covering is between the flap and the heat source.

2. The apparatus of claim 1 further comprising a strap coupled with the transportable case and formed into a shape substantially similar to an area of contact the user makes when sitting, the strap being foldable of a surface onto the transportable case, the strap providing an added insulating layer between the user and the heat source while allowing for a relatively greater heat transfer in areas immediately adjacent to the area of contact.

3. The apparatus of claim 2 wherein the strap is a U-shape having legs that meet at a trough, the legs being coupled with the transportable case opposite the trough, the trough having a slit therein to effect a deepening of the trough to increase an effective length of the legs when the user or another user wears the strap over a shoulder.

4. The system of claim 2 wherein the strap is a U-shape having legs that meet at a trough, the legs being coupled with the transportable case opposite the trough, the trough having a slit therein to effect a deepening of the trough to increase an effective length of the legs when the user or another user wears the strap over a shoulder.

5. The apparatus of claim 1 wherein the heat source is adapted to acquire heat by being microwaved in a microwave oven.

6. The apparatus of claim 1 wherein the transportable case includes elongated flaps having a first position to add or to provide a layer of insulation to the transportable case when the covering is in the first state and a second position wherein the elongated flaps are extended away from the case increasing a total surface area of the case when the covering is in the second state.

7. The apparatus of claim 1 wherein the case includes handles to enable the apparatus to be carried backpack style.

8. The apparatus of claim 1, wherein the canopy-like form is formed by wrapping the covering around a standing user and wherein the covering includes a pocket sized and shaped to receive the heat source to provide heat to within the canopy-like form.

9. The apparatus of claim 1 wherein the wherein the transportable case is sized and shaped to carry at least one additional item.

10. A system comprising:
    a fabric being of a size and shape suitable to be at least partially wrapped around a user and to be formed into a tent-like form being substantially enclosed at a top;
    a heating element; and
    a transportable case for encasing the fabric and the heating element and for holding the fabric and the heating element in heat transferring proximity to provide a first quantity of heat to the fabric from the heating element while adapted to be carried, the fabric providing at least a portion of the first quantity of heat to the user when wrapped around the user, and the heating element positionable below or within the tent-like form such that a second quantity of heat is provided to within the tent-like form from the heating element wherein the transportable case includes a multi position flap having a first position between the heating element and the fabric and a second position wherein the fabric is between the flap and the heating element.

11. The system of claim 10 further comprising a strap coupled with the transportable case and formed into a shape substantially similar to an area of contact the user makes when sitting, the strap being foldable onto a surface of the transportable case, the strap providing an added insulating layer between the user and the heating element while allowing for a relatively greater heat transfer in areas immediately adjacent to the area of contact.

12. The system of claim 10, wherein the tent-like form is formed by wrapping the covering around a standing user and wherein the covering includes a pocket sized and shaped to receive the heating element to provide heat to within the tent-like form.

13. An apparatus comprising:

a heat source;

a covering; and a transportable case sized and shaped to enclose the heat source and the covering in thermal transfer relation to warm the covering while the covering is in a first state, the covering having a second state, after being heated by the heat source in the first state, being at least partially wrapped around a user to partially warm the user from the heat provided thereto in the first state and formed into a canopy-like form being substantially enclosed at a top and wherein the heat source is positioned in relation to the canopy-like form to provide heat to within the canopy-like form, wherein the transportable case includes a multi position flap having a first position between the heat source and the covering and a second position wherein the covering is between the flap and the heat source.

14. A system comprising:

a fabric being of a size and shape suitable to be at least partially wrapped around a user and to be formed into a tent-like form being substantially enclosed at a top;

a heating element; and a transportable case for encasing the fabric and the heating element and for holding the fabric and the heating element in heat transferring proximity to provide a first quantity of heat to the fabric from the heating element, the fabric providing at least a portion of the first quantity of heat to the user when wrapped around the user, and the heating element positionable below or within the tent-like form such that a second quantity of heat is provided to within the tent-like form from the heating element, wherein the transportable case includes a multi position flap having a first position between the heating element and the fabric and a second position wherein the fabric is between the flap and the heating element.

* * * * *